United States Patent [19]

Schmidt, III

[11] Plant 4,392

[45] Mar. 6, 1979

[54] MAPLE TREE

[76] Inventor: J. Frank Schmidt, III, 14131 SE. 312th Ave., Boring, Oreg. 97009

[21] Appl. No.: 862,762

[22] Filed: Dec. 20, 1977

[51] Int. Cl.[2] ..... A01H 5/12

[52] U.S. Cl. ..... Plt./51

[58] Field of Search ..... Plt./51

*Primary Examiner*—Robert E. Bagwill

[57] ABSTRACT

This invention relates to a novel variety of Hedge Maple, distinguished by its upright branches and rapid initial rate of growth.

2 Drawing Figures

DESCRIPTION

The present invention relates to a new and distinct variety of maple tree of the species botanically known as *Acer campestre,* and commonly called "Hedge maple." I discovered my new variety as a seedling mutuation of unknown parentage which was growing in a cultivated area on land owned by my father in Gresham, Oreg.

While caring for this property, my attention was attracted to the new seedling because of its distinctive appearance caused by its upright branches. This upright habit of growth made my tree decidedly different from other trees of this species which typically have branches that project in widely varying directions from the tree trunk. Close observation of the new seedling and continued observations of the progeny thereof, subsequently asexually propagated by me in Boring, Oreg. by budding, confirmed that the unique upright growth habit of my new variety was a result of a seedling variation.

I am, therefore, convinced that my new tree represents a new and improved variety of *Acer campestre,* as particularly evidenced by the following unique combination of characteristics which have proven firmly fixed, are outstanding therein, and which distinguish it from all other varieties of this species:

(1) An upright habit of growth evidenced by branches which grow in a uniform, upright manner; and (2) a vigorous initial growth rate that results in my tree being taller than existing known varieties at the end of its first growing season.

The accompanying photographs depict the color of the foliage of my new variety as nearly true as is reasonably possible to make the same in color illustrations of this character.

FIG. 1 is a color photograph of the tree of the present invention taken late in August 1977 to show the upright appearance of the entire tree. The particular tree shown in this figure was budded during the summer of 1975.

FIG. 2 is a color photograph of leaves of the tree of my invention, taken at the same time as the photograph of FIG. 1. The smaller leaves in this figure were obtained from portions of branches in their second growing season while the larger leaves were obtained from portions of branches in their first growing season.

As previously indicated, the branches of my new variety grow in an upright manner. More specifically, the branches angle away from the trunk at an upward angle averaging approximately 45°. This upward growth habit gives my tree a pleasing balanced appearance. In contrast, known varieties of Hedge maple trees have branches that lack this characteristic of uniform upright growth. For example, it is not uncommon for a single tree to have both horizontal branches and branches that weep downwardly toward the ground.

In addition, my tree grows rapidly during its first year. To more specifically describe this characteristic, the first year's growth of twenty-seven trees of my new variety budded on *Acer campestre* understock were measured. To provide a more representative sample, the highest and lowest of these measurements were then deleted. The first year's growth of the remaining twenty-five trees ranged from about 147 cm. to 218 cm. and averaged close to 196 cm. For comparison purposes, a similar sampling was taken of the first year growth of *Acer campestre* seedlings growing in a row adjacent to the above measured trees of my new variety. The first year's growth of these seedlings ranged from about 135 cm. to about 183 cm. and averaged approximately 168 cm. Due to this more rapid first year growth, my new variety can be developed into a better tree. Hedge maples at my nursery are pruned at the end of their first growing season to remove branches from all but about the upper twenty inches of each tree. The remaining branches, called a "head", form the lowest branches of the tree as it develops. With my new variety, because of its rapid initial growth, the head is higher above the ground than in existing varieties. As a result, my new tree can be pruned after its first growing season in a manner that reduces the often undesirable shrub-like appearance of Hedge maple trees having their lowest branches closer to the ground.

Like known Hedge maples, the leaves growing from second year branches of my tree were smaller than the leaves growing from first year branches. However, the leaves of my new variety were somewhat larger than the leaves of other Hedge maples. Measurements of a sampling of leaves from first year branches of my new tree revealed the length of these leaves, from the base of the pedicle to the tip of the leaf, to be from about 5.4 to 14.2 cm. with an average length of about 8.8 centimeters. These leaves also ranged from about 3.5 to 8.7 cm. wide, with an average width of about 6 cm. Similar measurements of leaves from second year branches of my new variety showed that their length ranged from about 3.6 cm. to 12 cm., with an average of about 8.1 cm., and that their width ranged from 2.7 to 9.6 cm., with an average of about 7 cm. On the other hand, leaves taken from second year branches of Hedge maple seedlings growing in a row adjacent to the row containing the trees from which the above leaves were obtained, had a length ranging from about 4.4 to 10.7 cm. and averaging about 7.5 cm., and a width ranging from about 3.5 to 7.5 cm., and averaging 5.4 cm. In addition, leaves taken from first year branches of these seedling trees had a length ranging from about 5.5 to 13.6 cm. and averaging about 8.7 cm. and had a width ranging from about 5.0 to 8.8 cm. and averaging 6.5 cm. This sampling of leaf sizes is limited in that only about twenty-five to thirty leaves of each type were measured. However, it does generally confirm my observation that leaves of my new *Acer campestre* are somewhat larger than leaves of other known varieties.

Also, the foliage of my new tree appeared slightly darker than the foliage of other Hedge maples growing in an adjacent row. However, when an individual leaf from my variety was compared with a leaf from the other variety, the difference was not visible.

The following is a detailed description of my new variety of *Acer campestre* with color terminology in accordance with the "Royal Horticultural Society Color Chart" (hereinafter R.H.S.) published by the Royal Horticultural Society of London. It is pointed out, however, that the coloration of the leaves as indicated below is only approximate because the coloration varies during the growing season. In addition, the size and shape of the leaves varies from tree to tree and depends upon the nature of the growing season:

Parentage: A seedling mutation of unknown parentage.

Propagation: Holds to distinguishing characteristics through propagation by budding.

Locality where grown and observed: Gresham, Oreg. and Boring, Oreg.

Tree: Upright, healthy.

Branches: Grow uniformly upwardly from the tree trunk and have smooth bark.

Foliage:

*Shape.*—Palmate.

*Size.*—Leaves growing on first year branches typically range from 5 to 14 cm. long and 3.5 to 9 cm. broad. Leaves growing on second year branches typically range from about 3.5 to 12 cm. long and 2.5 to 10 cm. broad.

*Apex.*—Acute.

*Base.*—Rounded.

*Margin.*—Typically five lobes. The lobes are divided into secondary lobes by sinuses. Typically the margin of leaves growing from second year branches is entire while the margin of leaves growing from first year branches is wrinkled.

*Color.*—During the summer the leaves are a green color, somewhat like R.H.S. plate 147A.

I claim:

1. A new and distinct variety of maple tree substantially as herein shown and described, characterized particularly as to novelty by its upright branches and rapid initial rate of growth.

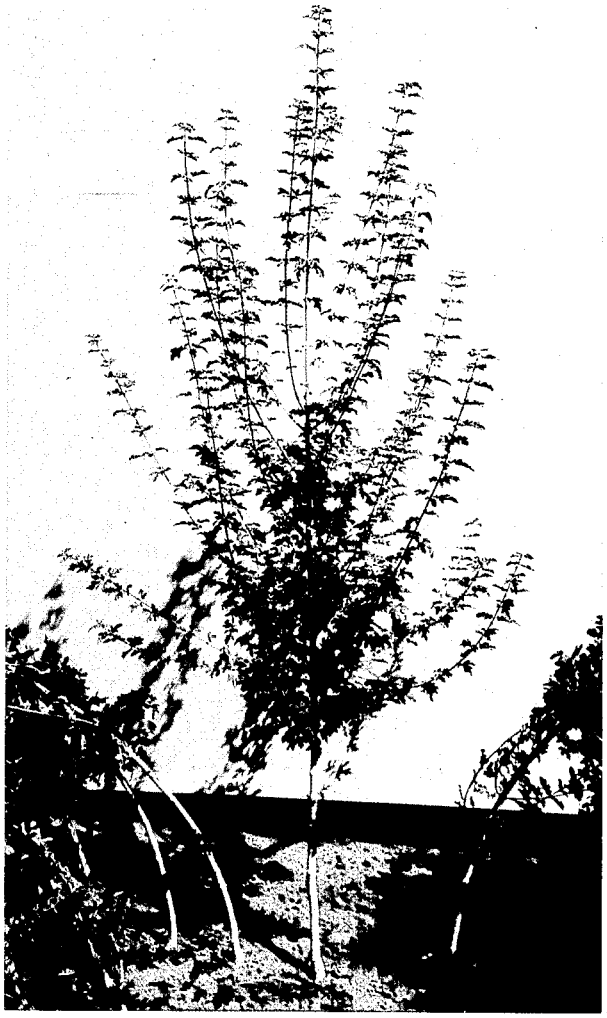
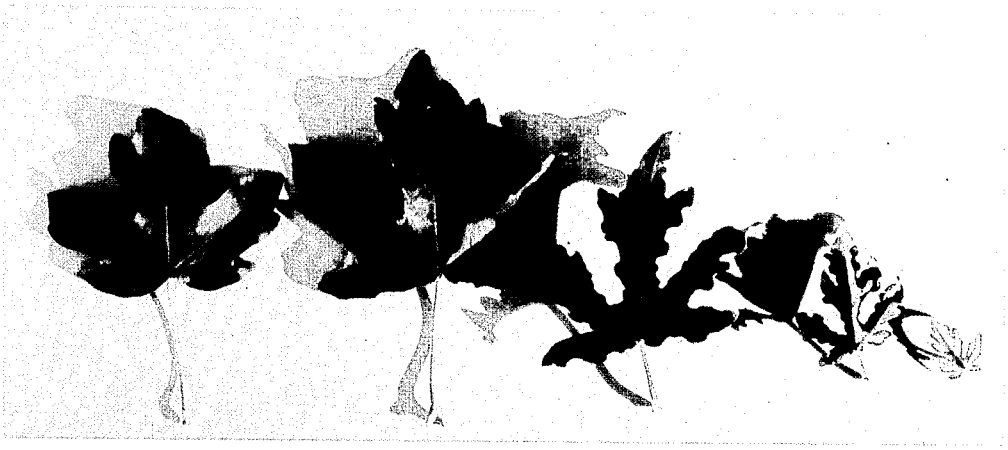

* * * * *